United States Patent [19]
Moreno et al.

[11] Patent Number: 5,328,485
[45] Date of Patent: Jul. 12, 1994

[54] DISPOSABLE SYRINGE WITH NEEDLE COVER

[76] Inventors: Saul Moreno; Jaime L. Szapiro; Leonardo Szames, all of Tabare 1641, Buenos Aires, Argentina

[21] Appl. No.: 106,389

[22] Filed: Aug. 13, 1993

[30] Foreign Application Priority Data

Aug. 20, 1992 [AR] Argentina ............................ 323,024

[51] Int. Cl.$^5$ ................................................. A61M 5/32
[52] U.S. Cl. ...................................... 604/198; 604/263
[58] Field of Search ............... 604/198, 187, 263, 192

[56] References Cited

U.S. PATENT DOCUMENTS

| 4,772,272 | 9/1988 | McFarland | 604/263 X |
| 4,816,022 | 3/1989 | Poncy | 604/198 |
| 5,222,947 | 6/1993 | D'Amico | 604/198 |

Primary Examiner—John D. Yasko
Attorney, Agent, or Firm—Bachman & LaPointe

[57] ABSTRACT

Disposable syringe with needle cover including a slidable needle cover preventing contact of the user with the needle and preventing re-use of the assembly.

5 Claims, 1 Drawing Sheet

DISPOSABLE SYRINGE WITH NEEDLE COVER

BACKGROUND OF THE INVENTION

The instant invention relates to a disposable syringe with needle cover, of the type ready to be used; the needle and its corresponding protecting sheath as well as the remaining parts and forming elements being also ready to be used and being sterilized. The advantage of the syringe of the invention is that the user will have no contact with the needle or surrounding regions, before, during and after the injection; the assembly being completely disabled thereafter.

More particularly, the instant invention relates to a syringe of the above mentioned type comprised by a main cylindrical, hollow body, having a solid plunger displacing therein, which is located coaxially, the inner space of said cylindrical main body constituting the transient housing of the liquid or medicine to be injected, as well as of blood or other liquids to be withdrawn from the body, in accordance with the displacement direction of such plunger.

PRIOR ART

As already known, such main cylindrical body has a wholly opened base defining an opening from which the rear end of said coaxial plunger projects, such plunger being characterized by having an annular flange in order that the user may push or pull manually the plunger, according to the desired action. The inner end or head of the plunger tightly fits inside the walls and at the bottom of said main body, such that the variable volume chamber defined therein is always tight and isolated from the outside. Said bottom has, in turn, an outer frusto-conical hollow and coaxial nozzle converging towards its outer end, constituting the plugging means for coupling and fixing the injection needle.

This conical coupling means is standard in conventional syringes and is called "plugging cone" or "luer cone". To this end, needles which may be placed separately, housed inside a protecting sheath keeping them duly isolated and sterilized, have at their rear end the corresponding coupling means integral with the needle, such coupling means having its inner surface mating with said plug at the "luer cone", while the outer surface serves for removably coupling said sheath protecting the needle.

Considering the highly contagious diseases, specially those being transmitting through blood, the present approach is to attain disposable and disabled syringes, thus assuring whole sterility and reliance to patients. Several embodiments are already known in which the syringe and needle are disabled after their use.

Nevertheless, there is no embodiment protecting and assuring the impossibility of infection to the person applying the injection to the patient, specially taking into account that such person is that handling the syringe with the risk of an undesired puncture or of contacting small blood droplets from the patient when introducing or withdrawing the needle. When injecting with known syringes, the assembly is withdrawn pulling outward syringe and needle. In this way, accidental punctures may occur, thus causing leakages of blood or of the liquid injected on the patient's skin, on the hands of the user, on clothes or other elements used for applying the injection, all of which may imply contamination.

SUMMARY OF THE INVENTION

The syringe of the instant invention offers an efficient solution to both problems. Its constructive features prevent the possibility of re-use and include simultaneously a shiftable needle cover avoiding all contact of the user with the needle. In fact, such needle cover is an end cylindrical body coaxially surrounding the main body, being shiftable longitudinally therealong, until it is located as axial projection of the syringe along a portion long enough such as to house the needle used, without any risk of dangerous leaks; further, handling of the syringe will be safe, avoiding accidental punctures, splits or other dangerous situations.

The invention also includes an insert between the syringe plugging cone and the needle plugging cone. This insert has two essential features influencing the general operation of the syringe: the first is that, being coupled to the upper end of the syringe, it provides the standard "luer cone" for coupling the needle and, the second one is that it has an outer annular flange engaged to inner lower retention means of the needle cover, such that, after the injection is effected, when the needle cover is withdrawn and disposed, this cover entraps the needle which is retained by such means. It is clear that the user may never contact the needle.

Further, the insert, as mentioned, is that having the "luer cone" and not the syringe. Therefore, the syringe is also disabled and cannot be used again since it does not longer have the proper plugging cone for receiving a conventional needle.

BRIEF DESCRIPTION OF THE DRAWINGS

A preferred, non-limiting, embodiment of the invention will be hereinbelow described in connection with the accompanying drawings, in which.

In all figures, the same reference numerals designate the same or equivalent elements.

DETAILED DESCRIPTION OF THE INVENTION

Figure 1:
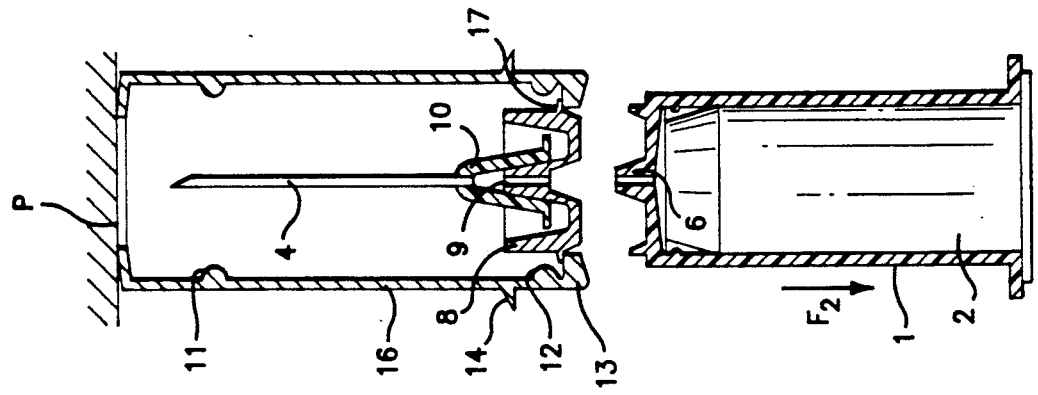
FIG. 1 is a longitudinal and axial section of a disposable syringe with needle cover, before being used, according to the instant invention.

As may be seen in all figures, the syringe is comprised by a main hollow cylindrical body 1, a plunger penetrating and displacing tightly through the open end of the body 1, thus defining a variable volume chamber 3, which is filled with the liquid or medicine to be injected to the patient, using the needle 4 to this end.

The novelty of the invention resides in the needle coupling along with the use of a needle cover.

In fact, said main body 1 has at its closed end, opposed to the mouth, a small conical nozzle 6 and an annular wall having a diverging inner surface 7 defining the pressure, removable seating means of a novel and particular insert 8, in which a plugging cone is located 9, whose dimensions are those established for the removable coupling of the needle through its integral joining means 10.

The conical nozzle 6, as well as the plugging cone 9, have an inner conduit axially communicating with the interior of the main body 1, wherein the liquid to be injected is contained.

The assembly also has an outer cylindrical needle cover 15 which is coaxial to the main body 1 and the plunger 2 which has a longer length and is shiftable with respect to said main body; having in turn two inner lower annular projections 12 and 13 constituting means for retaining the insert 8, as will be explained hereinbelow, as well as an upper inner annular flange 11 holding the insert in a stable position prior to use and, finally, a lower and outer annular lug 14 is provided in order that the user may displace the needle cover with respect to the main body, or vice-versa, i.e. displace the main body with respect to the needle cover.

Figure 2:
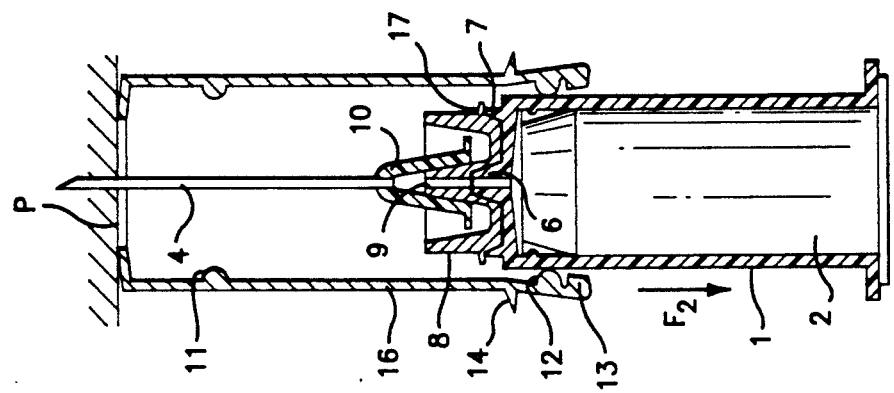
FIG. 2 is a section similar to that of FIG. 1, showing the forming elements, with the needle already applied to the patient and the syringe plunger in a position for injecting the liquid product.

The user, after removing sheath 15 protecting needle 4, introduces the needle into a patient P, as shown in FIG. 2, after which, bearing the front end of the needle cover on the patient's skin, the medicine is injected displacing plunger 2 in the direction F1.

Figure 3:
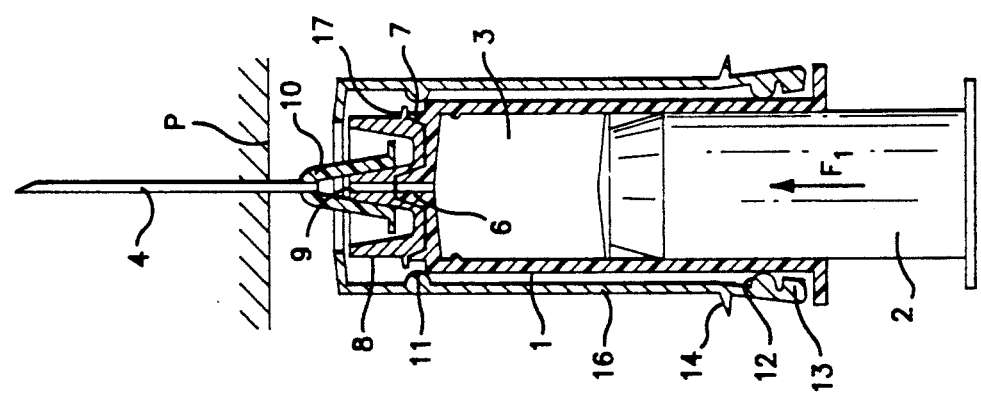
FIG. 3 is the same section, but indicating the way in which the needle cover acts during the withdrawal action of the syringe.

With reference to FIG. 3, the novel protecting action of this embodiment may be seen. Through the use of the mentioned annular lug 14, the user retains the needle cover 10 on the patient's skin and displaces outwardly and simultaneously the needle 4 and the main body 1, which are engaged; this is carried out by a movement in the direction indicated at F2. In this step, the needle is integral to the main body through the action of said insert 8 engaging both elements as mentioned above and shown in the three first figures.

It is clear, from FIG. 3, that any undesired splash produced along with the removal of said needle is confined at the interior of the needle cover 16, preventing any possibility of contact with the user.

Figure 4:
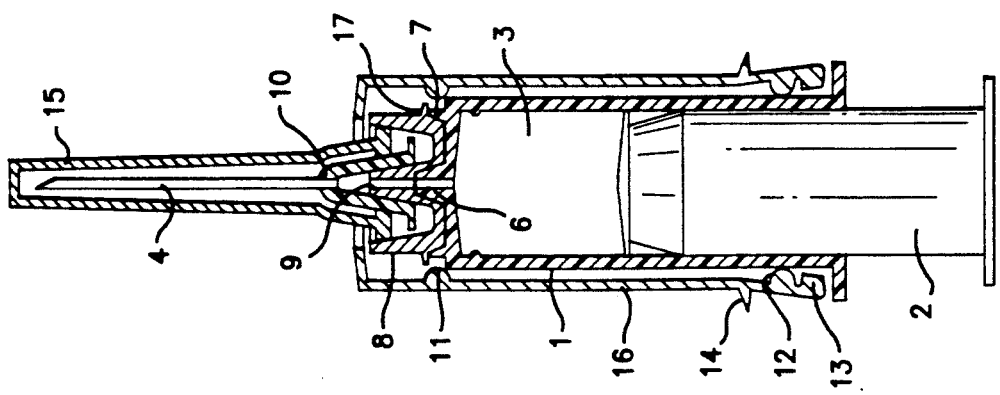
FIG. 4 is another longitudinal section, similar to former ones, indicating the way in which the two main portions of the syringe of the invention are separated and disabled.

With reference to FIG. 4, the operation of the syringe of the invention at the last step of the injection may be understood. Maintaining the needle cover 16 on the patient's skin, the main body is displaced 1 in the direction indicated by F2, which produces withdrawal of said main body 1 with respect to the needle, since insert 8 offers a very low resistance to traction in this direction. Simultaneously, the same insert 8 is retained at the inner space of the needle cover the user having not contacted the needle. To this end, projections 12, 13 act along with an annular flange 17 of the novel insert 8.

Therefore, the disposable feature of the syringe of the invention may be understood by the use of the needle cover 16 along with insert 8 which, as mentioned above, forms a "luer" standard cone capable of retaining the needle 4 by plugging and, in turn, cone 9 has a special shape in its inner conical cavity allowing the removable coupling on said conical nozzle 6 of the main body.

Measures and proportions of conical nozzle 6 are not the conventional ones for retaining injection needles such that, said separated syringe portion may not be used again since it is impossible to place another needle thereon.

Regarding retention elements designated with reference numerals 11, 12, 13, 7 and 17, it is to be note that they correspond to a constructive embodiment chosen as example of the invention, but equivalent resources may be used for the same function.

It will also be noted that in FIGS. 1, 2 and 3, the lower portion of the needle cover, wherein retention means 12 and 13 are located, the needle cover body has a slightly diverging shape, since it has a compressive resilient tendency in order to cooperate with coupling and retention of insert 8; which, upon being withdrawn from the main body 1, confines its annular flange 17 between said means 12 and 13.

We claim:

1. A disposable syringe with needle cover of the type comprising, in combination, a straight axis cylindrical main hollow body, shiftably and tightly housing a plunger passing through the lower open end thereof, while from the center of the opposed end a conical and coaxial hollow nozzle projects, the inner conduit of which communicates to the interior of the needle coupling means, wherein, between said coaxial hollow nozzle of the main hollow body and the needle coupling means there is a coaxial insert having a standard plugging cone at its central region; said insert being housed in the interior of a hollow, shiftable and coaxial hollow needle cover, having a length longer than the needle plus its coupling means, and of a length greater than that of the main body; said needle cover having a wholly opened lower end as well as means for being removably retained with respect of the main body and means for retaining the coaxial insert, wherein said coaxial hollow nozzle of the main cylindrical body is surrounded by an annular wall, the inner surface of which is conical, a peripheral cavity being defined with respect to said nozzle, the size of which is slightly smaller than the peripheral annular portion defined around the plugging cone of the coaxial insert.

2. A disposable syringe as claimed in claim 1, wherein means for removably retaining the needle cover of the main body are a lower, outer annular flange, of a diameter higher than the lower hollow end diameter of the needle cover, along with an inner upper annular projection defined at the needle cover, the diameter of which is slightly greater than the outer diameter of the main cylindrical body.

3. A disposable syringe as claimed in claims 1 wherein said coaxial insert plugging cone has an inner shape similar to said upper hollow nozzle of the main body and slightly smaller than that of said nozzle.

4. A disposable syringe as claimed in claim 1, wherein the outer shape of the plugging cone of the coaxial insert is slightly smaller than the standard coupling means of the needle and similar thereto.

5. A disposable syringe as claimed in claim 1, wherein the means for retaining the coaxial insert of the needle cover comprises two inner annular projections defined adjacent its lower end, separation of which allows the tight housing of the outer annular flange of said insert.

* * * * *